US010183134B2

(12) United States Patent
Ikei et al.

(10) Patent No.: US 10,183,134 B2
(45) Date of Patent: *Jan. 22, 2019

(54) INSUFFLATION/EXSUFFLATION AIRWAY CLEARANCE APPARATUS

(71) Applicant: Hill-Rom Services Pte. Ltd., Singapore (SG)

(72) Inventors: Christopher Ikei, Parker, CO (US); Dano S. Carbone, Lakewood, CO (US); Lewis W. Ward, Boulder, CO (US); Tammy Stultz, Westminster, CO (US)

(73) Assignee: Hill-Rom Services Pte. Ltd., Singapore (SG)

( * ) Notice: Subject to any disclaimer, the term of this patent is extended or adjusted under 35 U.S.C. 154(b) by 846 days.

This patent is subject to a terminal disclaimer.

(21) Appl. No.: 14/630,104

(22) Filed: Feb. 24, 2015

(65) Prior Publication Data
US 2015/0174350 A1 Jun. 25, 2015

Related U.S. Application Data

(63) Continuation of application No. 13/957,473, filed on Aug. 2, 2013, now Pat. No. 8,985,112, which is a
(Continued)

(51) Int. Cl.
*A61M 16/00* (2006.01)
*A61M 16/20* (2006.01)
(Continued)

(52) U.S. Cl.
CPC ........ *A61M 16/0066* (2013.01); *A61M 16/00* (2013.01); *A61M 16/0003* (2014.02);
(Continued)

(58) Field of Classification Search
CPC .... A61M 16/20; A61M 16/00; A61M 16/208; A61M 16/0066; A61M 2205/3368;
(Continued)

(56) References Cited

U.S. PATENT DOCUMENTS 2,523,844 A 12/1950 Emerson
2,918,917 A 12/1959 Emerson
(Continued)

FOREIGN PATENT DOCUMENTS

EP 1897597 A2 3/2008
WO WO 2002/058619 A2 8/2002
(Continued)

OTHER PUBLICATIONS

Respironics, Cough Assist User Guide, Apr. 24, 2008.
(Continued)

*Primary Examiner* — Steven Douglas
(74) *Attorney, Agent, or Firm* — Barnes & Thornburg LLP

(57) ABSTRACT

An MIE apparatus has a blower, a valve system, and a mask hose connector. The blower is connected to the valve system which is connected to the hose connector. During insufflation, the valve system connects exhaust of the blower to the hose connector to cause positive pressure at the hose connector. During exsufflation, the valve system connects the blower intake to the hose connector to cause negative pressure at the hose connector. The apparatus has an automatic mode in which switching between insufflation and exsufflation is based on one or more preset time intervals and a manual mode in which switching between insufflation and exsufflation is based on a manual input from a user.

15 Claims, 8 Drawing Sheets

Related U.S. Application Data continuation of application No. 13/107,463, filed on May 13, 2011, now Pat. No. 8,539,952.

(51) Int. Cl.
*A61M 16/06* (2006.01)
*A61M 16/08* (2006.01)
*A61M 16/10* (2006.01)

(52) U.S. Cl.
CPC .... *A61M 16/0006* (2014.02); *A61M 16/0009* (2014.02); *A61M 16/0069* (2014.02); *A61M 16/06* (2013.01); *A61M 16/0816* (2013.01); *A61M 16/20* (2013.01); *A61M 16/202* (2014.02); *A61M 16/205* (2014.02); *A61M 16/107* (2014.02); *A61M 2016/0027* (2013.01); *A61M 2205/3331* (2013.01); *A61M 2205/3368* (2013.01); *A61M 2205/502* (2013.01); *A61M 2205/505* (2013.01); *A61M 2209/06* (2013.01)

(58) Field of Classification Search
CPC ............ A61M 2205/505; A61M 16/06; A61M 16/0006; A61M 16/202; A61M 2016/0027; A61M 16/0003; A61M 16/0816; A61M 2205/3331; A61M 2205/502; A61M 16/0069; A61M 16/0009; A61M 16/107; A61M 16/205
See application file for complete search history.

(56) References Cited

U.S. PATENT DOCUMENTS

| | | | |
|---|---|---|---|
| 4,054,134 A | 10/1977 | Kritzer | |
| 4,062,358 A | 12/1977 | Kritzer | |
| 4,226,233 A | 10/1980 | Kritzer | |
| 4,719,910 A | 1/1988 | Jensen | |
| 4,805,612 A | 2/1989 | Jensen | |
| 4,821,709 A | 4/1989 | Jensen | |
| 5,704,346 A | 1/1998 | Inoue | |
| 6,102,042 A | 8/2000 | Hete et al. | |
| 6,176,235 B1 | 1/2001 | Benarrouch et al. | |
| 6,209,540 B1 | 4/2001 | Sugiura et al. | |
| 6,213,119 B1 | 4/2001 | Brydon et al. | |
| 6,332,463 B1 | 12/2001 | Farrugia et al. | |
| 6,345,619 B1 | 2/2002 | Finn | |
| 6,526,970 B2 | 3/2003 | DeVries et al. | |
| 6,543,449 B1 | 4/2003 | Woodring et al. | |
| 6,622,724 B1 | 9/2003 | Truitt et al. | |
| 6,666,209 B2 | 12/2003 | Bennett et al. | |
| 6,694,978 B1 | 2/2004 | Bennarsten | |
| 6,702,769 B1 | 3/2004 | Fowler-Hawkins | |
| 6,708,600 B2 | 3/2004 | Hete et al. | |
| 6,877,511 B2 | 4/2005 | DeVries et al. | |
| 6,899,100 B2 | 5/2005 | Wickham et al. | |
| 6,929,007 B2 | 8/2005 | Emerson | |
| 6,932,084 B2 | 8/2005 | Estes et al. | |
| 6,984,214 B2 | 1/2006 | Fowler-Hawkins | |
| 7,044,129 B1 | 5/2006 | Truschel et al. | |
| 7,096,866 B2 | 8/2006 | Be'eri et al. | |
| 7,152,598 B2 | 12/2006 | Morris et al. | |
| 7,210,478 B2 | 5/2007 | Banner et al. | |
| 7,225,809 B1 | 6/2007 | Bowen et al. | |
| 7,343,917 B2 | 3/2008 | Jones | |
| 7,448,383 B2 | 11/2008 | Delache et al. | |
| 7,770,580 B2 | 8/2010 | Kruger et al. | |
| 7,836,881 B2 | 11/2010 | Lurie et al. | |
| 8,025,054 B2 | 9/2011 | Dunsmore et al. | |
| 8,066,004 B2 | 11/2011 | Morris et al. | |
| 8,074,647 B2 | 12/2011 | Truitt et al. | |
| 8,302,602 B2 | 11/2012 | Andrieux et al. | |
| 8,365,727 B2 | 2/2013 | Dunsmore et al. | |
| 8,397,722 B2 | 3/2013 | Berthon-Jones et al. | |
| 8,424,514 B2 | 4/2013 | Oates et al. | |
| 8,539,852 B2 | 9/2013 | Yamamura | |
| 8,539,952 B2 | 9/2013 | Carbone et al. | |
| 8,985,112 B2 | 3/2015 | Ikei et al. | |
| 2005/0039749 A1 | 2/2005 | Emerson | |
| 2005/0051174 A1 | 3/2005 | Emerson | |
| 2006/0130835 A1 | 6/2006 | Truschel et al. | |
| 2007/0017522 A1 | 1/2007 | Be-Eri et al. | |
| 2007/0186928 A1 | 8/2007 | Be'eri | |
| 2008/0202528 A1 | 8/2008 | Carter et al. | |
| 2008/0264419 A1 | 10/2008 | Lomask et al. | |
| 2008/0283060 A1 | 11/2008 | Bassin | |
| 2009/0126734 A1 | 5/2009 | Dunsmore et al. | |
| 2010/0180897 A1 | 7/2010 | Malgouyres | |
| 2010/0312751 A1 | 12/2010 | Anglin et al. | |
| 2011/0220107 A1 | 9/2011 | Kimm et al. | |

FOREIGN PATENT DOCUMENTS

| | | |
|---|---|---|
| WO | WO 2003/005886 A2 | 1/2003 |
| WO | WO 2003002176 A2 | 1/2003 |
| WO | WO 2006/004439 A2 | 1/2006 |
| WO | WO 2007/055829 A2 | 5/2007 |
| WO | WO 2010/000439 A1 | 1/2010 |

OTHER PUBLICATIONS

Tatkov, Stanislav et al., "Symmetrical-Waveform High-Frequency Oscillation Increases Artificial Mucus Flow Without Changing Basal Mucus Transport in In Vitro Ovine Trachea," 435 Respiratory Care, vol. 56, No. 4 (Apr. 2011).
Great Ormond Street Hospital for Children NHS Trust, The RC Comet Information for Families, 2010.
International Search Report and Written Opinion for PCT/US2012/036876, dated Nov. 26, 2012, 8 pages.
Supplementary European Search Report, dated Jul. 29, 2014, in related case, EP 12786272, 9 pages.
Dima Italia SRL. Mini Pegaso Cough brochure.

INSUFFLATION/EXSUFFLATION AIRWAY CLEARANCE APPARATUS

CROSS-REFERENCE TO RELATED APPLICATIONS

This application is a continuation of U.S. application Ser. No. 13/957,473, filed Aug. 2, 2013, now U.S. Pat. No. 8,985,112, which is a continuation of U.S. application Ser. No. 13/107,463, filed May 13, 2011, now U.S. Pat. No. 8,539,952, each of which is hereby expressly incorporated by reference herein in its entirety.

BACKGROUND OF THE INVENTION

1. Field of the Invention

The present invention relates to medical devices, more particularly, to devices that aid in breathing and in inducing coughs.

2. Description of the Related Art

Professionals using mechanical Insufflators/Exsufflators (MIEs) have realized over the years that there are serious limitations to current machines. There have been no real improvement in MEI functionality in 50 years.

Parents of pediatric patients, as well as many adult patients, take the machine everywhere with them. Size and weight are a problem.

MEIs typically operated on 120 volts AC. In order to operate in many vehicles with a 12 volt DC system, inverters have to be installed, which are expensive and complicated to install.

A major concern of the medical community is the use of an MIE on sicker patients with compromised lung function and reduced functional residual capacity because current MIEs do not incorporate positive end expiratory pressure on the expiratory phase.

For many patients with thick secretions, current MIEs need a great amount of time and additional intervention to mobilize and remove them.

Many pediatric, elderly, and stroke patients have difficulty synchronizing with the breathing pattern of the current MIEs.

BRIEF SUMMARY OF THE INVENTION

The MIE apparatus of the present invention has a case that houses an adjustable speed blower, a valve subassembly with a direction valve and an oscillator, a hose connector, a controller, a power supply, and a touch screen.

The blower intake is connected to an intake port on the direction valve and the blower exhaust is connected to the exhaust port on the direction valve. The common port of the direction valve is connected to the valve port of the oscillator and the connector port of the oscillator is connected to the mask hose connector. The air flow path between the blower and the hose connector is the channel.

The apparatus has two primary modes: insufflation and exsufflation. In insufflation mode, the direction valve connects the blower exhaust to the oscillator, causing positive pressure at the hose connector. In exsufflation mode, the direction valve connects the blower intake to the oscillator, causing negative pressure at the hose connector. To induce a cough, the apparatus starts in the insufflation mode to fill the lungs and then quickly switches to exsufflation mode, rapidly deflating the lungs and thereby stimulating a cough.

The oscillator is a butterfly valve with a chamber and a 360° rotating disc within the chamber. During the insufflation, the disc is rotated to a stationary position of high, medium, or low flow rate to modulate the airflow. In the high position, the disc is parallel to the channel and, at the low flow rate, the disc is almost perpendicular to the channel.

During exsufflation, the oscillator is either inactive or is in a "flutter" mode. If inactive, the disc is parallel to the channel to maximize airflow. In flutter mode, the disc is continuously rotated, causing the channel size to rapidly change from a maximum flow rate to minimal flow rate and back.

The apparatus can operation in manual mode or automatic mode. In manual mode, the user controls when and how a treatment cycle occurs by pressing the associated buttons on the touch screen or on the remote control. In automatic mode, the apparatus repeatedly initiates treatment cycles, which is an insufflation followed by an exsufflation followed by a rest.

For manual mode, the insufflation pressure, the exsufflation pressure, the rest pressure, the flow rate, and the flutter frequency can be set. For automatic mode, in addition to the manual mode parameters, the insufflation time, the exsufflation time, the rest time, and the number of cycles can be set.

In manual mode, the patient touches a start/stop button to turn the blower on. An insufflation is initiated by actuating an inhale button on the touch screen or remote and is maintained until the button is released. An exsufflation is initiated by actuating an exhale button on the touch screen or remote and is maintained until the button is released. When treatment is complete, the patient touches a start/stop button to turn the blower off.

In automatic mode, the patient touches a start/stop button to turn the blower on and to begin the treatment cycles. When the set number of the treatment cycles is reached, the apparatus discontinues treatment and turns the blower off.

BRIEF DESCRIPTION OF THE DRAWINGS

For a fuller understanding of the nature and object of the present invention, reference is made to the accompanying drawings, wherein.

DETAILED DESCRIPTION OF THE INVENTION

Figure 1:
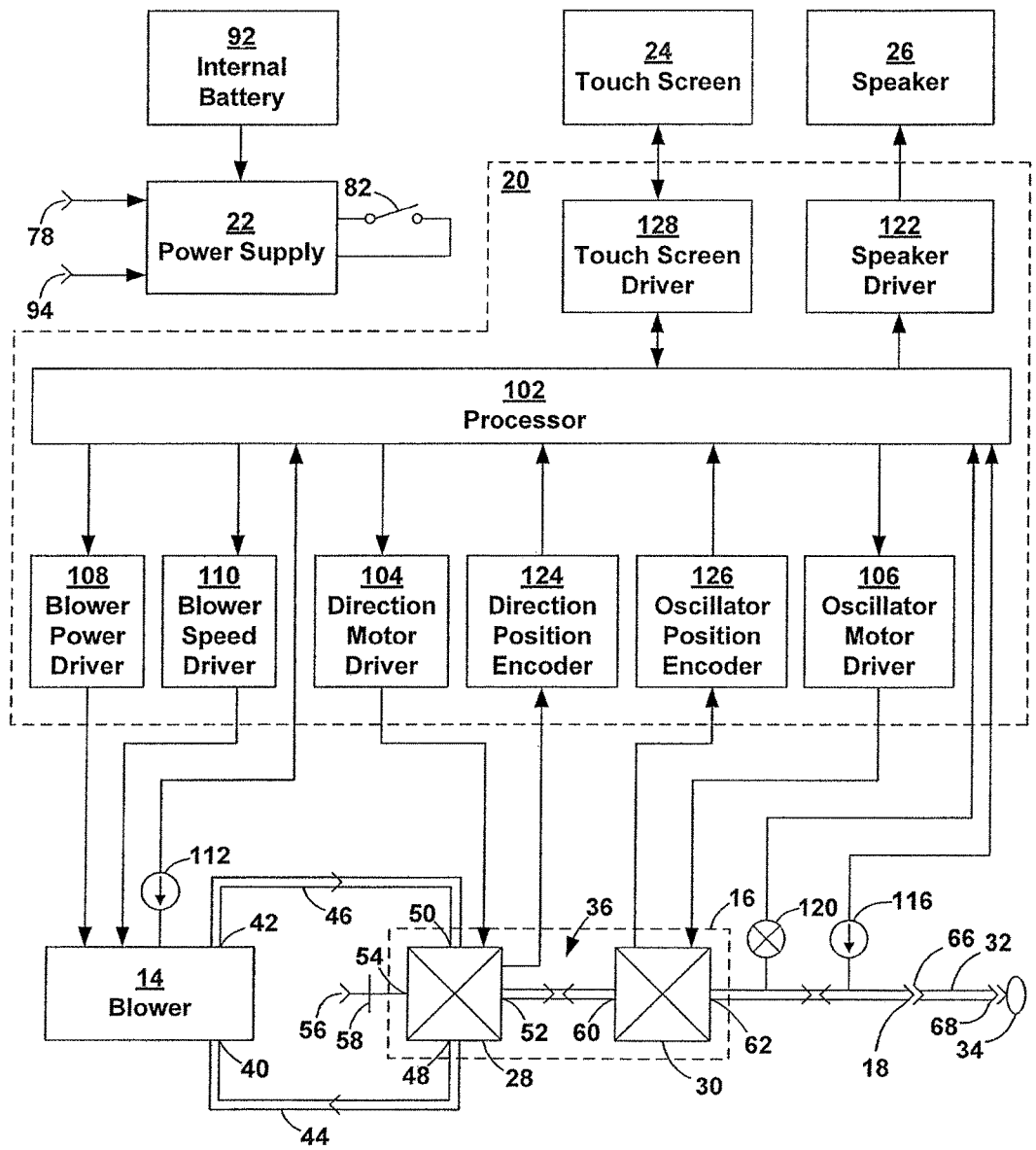
FIG. 1 is a schematic diagram of the apparatus of the present invention.
Figure 2:
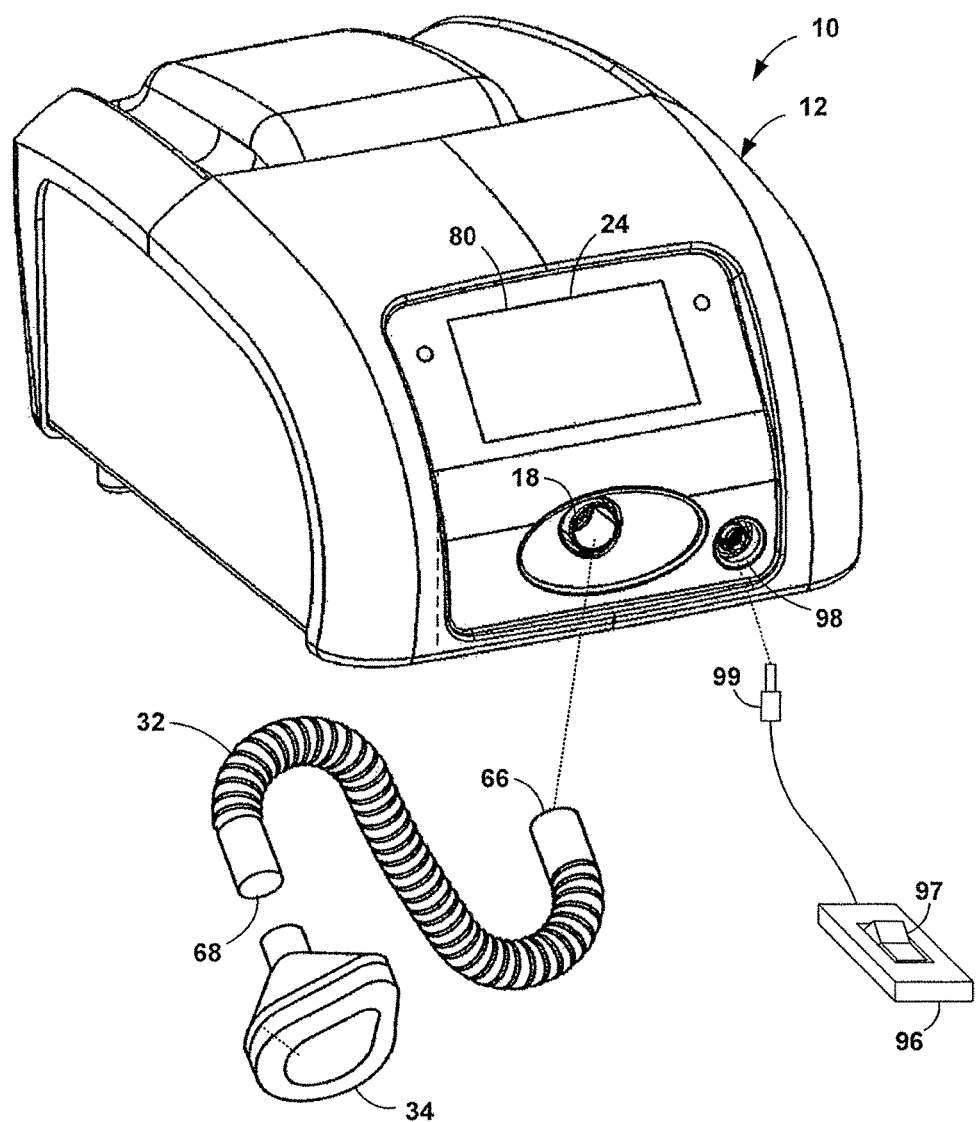
FIG. 2 is a front, perspective view of the apparatus.
Figure 3:
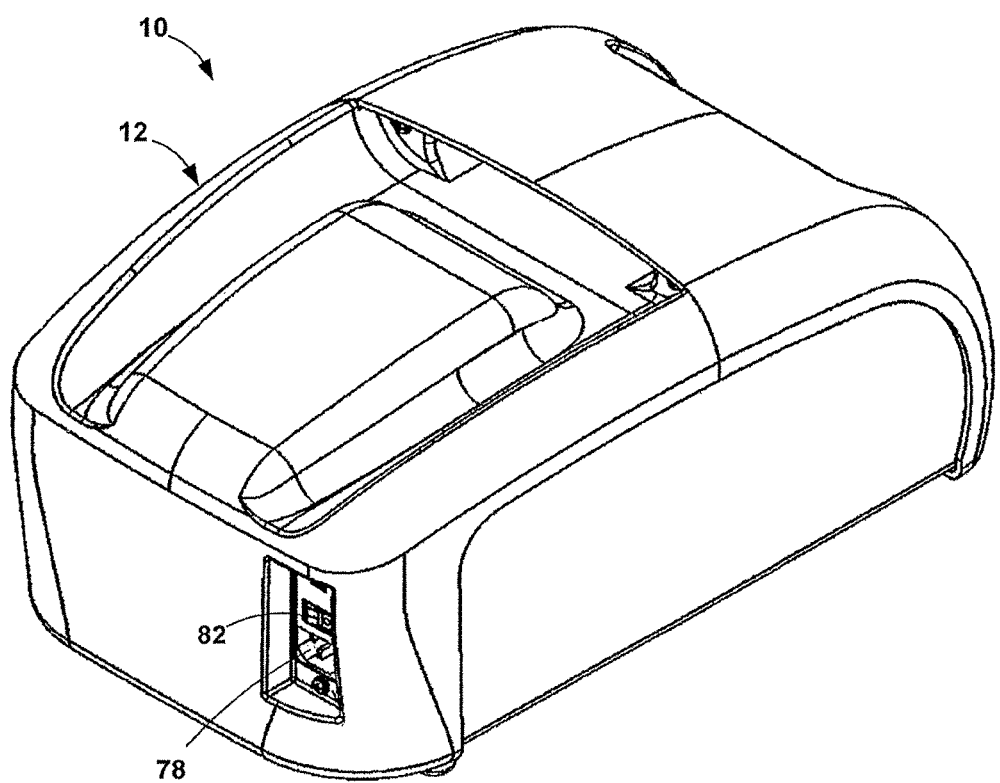
FIG. 3 is a back view of the apparatus of FIG. 2.
Figure 4:
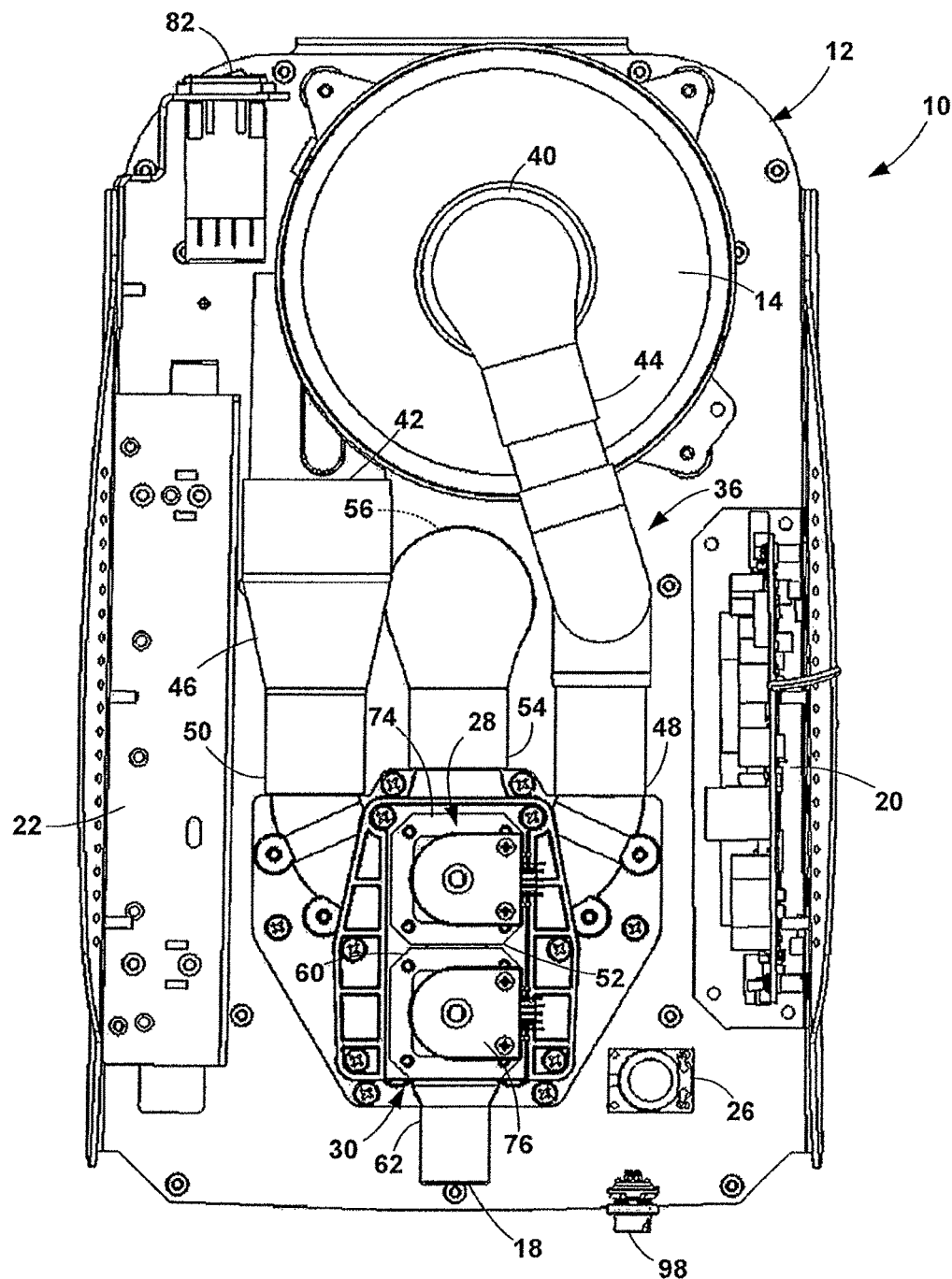
FIG. 4 is top view with the case top removed.
Figure 5:
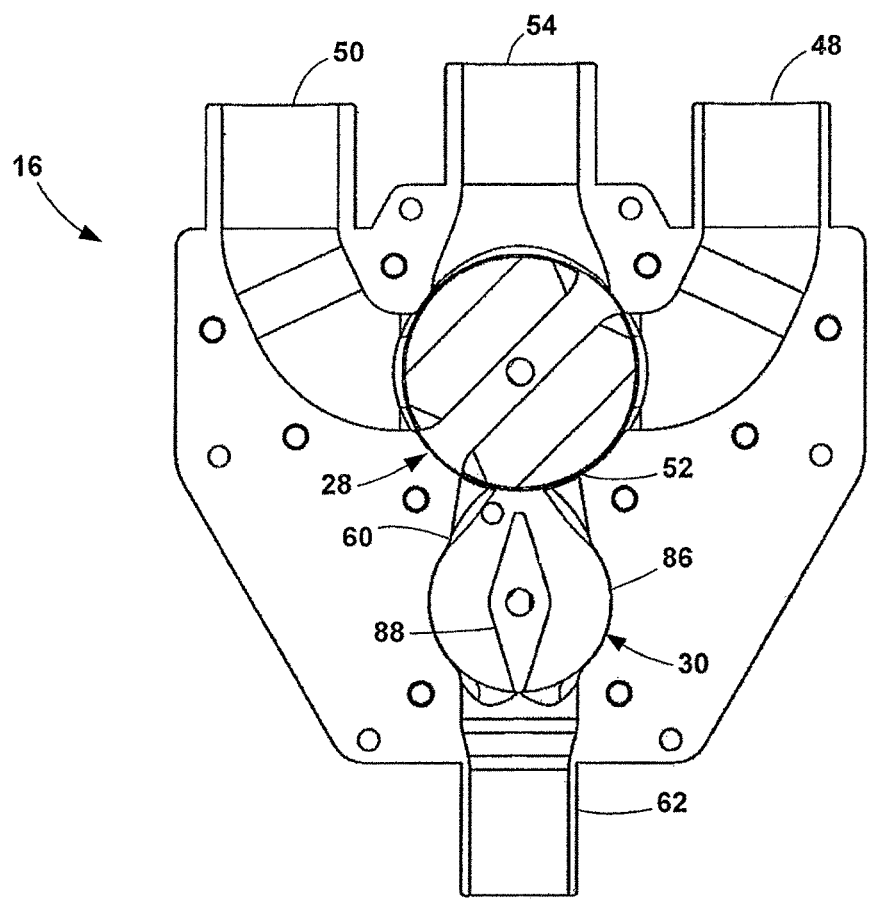
FIG. 5 is a top, cross-sectional view of the valve subassembly.
Figure 6:
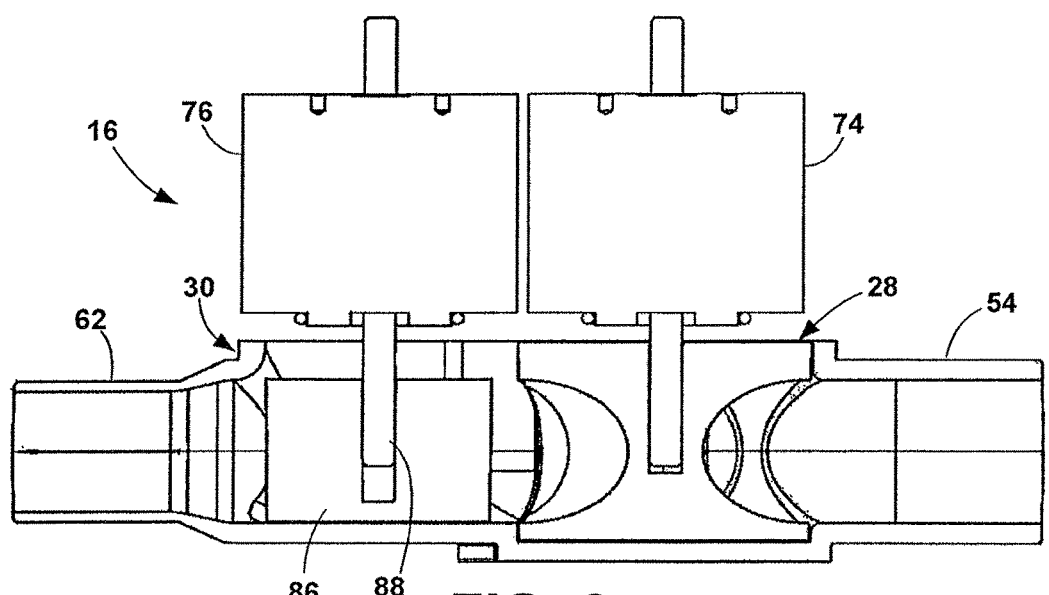
FIG. 6 is a side, cross-sectional view of the valve subassembly.

The present invention is an apparatus for assisting in coughing. One feature of the present invention is the ability to vibrate the airway. Vibration of the airway at a specific frequency creates the phenomenon known as "enhanced diffusivity". This mechanism changes the rate of diffusion in the alveolar-capillary membrane of the lung. By changing the diffusion coefficient in the lung, greater amounts of oxygen can be put into the blood stream and greater amounts of carbon dioxide can be removed. The special valve that creates this function is a rotating butterfly-type mechanism which has an adjustable frequency for conforming to specific pulmonary physiologies.

Another feature is the ability to use the apparatus to recruit lung volume. The apparatus uses a mechanism to gradually adjust the base pressure at the end of exsufflation. This creates a degree of positive pressure inside the lung thereby helping the lung to reinflate when vital capacity has been decreased due to pulmonary compromise. The base pressure is adjustable from 0 to 15 cm $H_2O$ depending on the degree of compromise The cough assist apparatus 10 of the present invention is shown in FIGS. 1-9. The case 12 houses a blower 14, a valve subassembly 16, a hose connector 18, a controller 20, a power supply 22, and a touch screen 24. The valve subassembly 16 includes a direction valve 28 and an oscillator 30.

An overall diagram of the apparatus 10 is shown in FIG. 1. The blower 14 has an intake 40 where air enters the blower 14 and an exhaust 42 where air exits the blower 14. The blower intake 40 is connected to the intake port 48 of direction valve 28 via an intake duct 44. The blower exhaust 42 is connected to the exhaust port 50 of the direction valve 28 via an exhaust duct 46. The common port 52 of the direction valve 28 is connected to the valve port 60 of the oscillator 30. The atmosphere port 54 of the direction valve 28 is open to atmosphere, as at 56, and has an optional filter 58. The connector port 62 of the oscillator 30 is connected to the patient interface (mask) hose connector 18. The path of air flow between the blower 14 and the hose connector 18 is referred to as the channel 36. The controller 20 controls the operation of the apparatus 10. A power supply 20 provides power to the components. Each component of the apparatus 10 is described in detail below.

When in use, a hose 32 is attached to the apparatus 10. One end 66 of the hose 32 attaches to the apparatus 10 at the hose connector 18. The mask 34 is attached to the other end 68 of the hose 32.

The apparatus 10 has two primary modes: insufflation and exsufflation, that is, inhale and exhale relative to the patient. To induce a cough, the apparatus 10 starts in the insufflation mode to fill the lungs. The apparatus 10 then rapidly transitions to exsufflation mode, rapidly deflating the lungs and thereby stimulating a cough.

The case 12 houses and protects the operational components of the apparatus 10. Accessible from the outside of the case 12 are the touch screen 24, hose connector 18, remote control connector 98, a power input connector 78, and power switch 82. Optionally, the touch screen 24 has a resilient protective cover 80.

The blower 14 used in the present configuration is a standard motorized blower with an adjustable speed. It has an intake 40 for suction and an exhaust 42 for blowing. The speed of the blower 14 is controlled by varying the voltage at a control input. The blower 14 is capable of providing a flow rate of up to 12.4 liters/sec.

The setting of the direction valve 28 determines the direction of airflow to the hose connector 18 and, ultimately, the mask 34. In insufflation mode, the direction valve 28 connects the blower exhaust 42 to the oscillator 30, causing a positive flow at the hose connector 18, and connects the blower intake 40 to atmosphere, as at 56, as a source of air for the blower 14. In exsufflation mode, the direction valve 28 connects the blower intake 40 to the oscillator 30, causing a negative flow at the hose connector 18, and connects the blower exhaust 42 to atmosphere, as at 56, for pressure relief. The controller 20 operates the direction valve 28 by a two-position stepper motor 74.

The oscillator 30 is a butterfly valve with a chamber 86 between the valve port 60 and connector port 62 and a rotating disc 88 within the chamber 86. The disc 88 rotates 360° and is controlled by the controller 20 using a stepper motor 76. The controller 20 modulates the opening of the channel 36 by rotating the disc 88 to various positions. The stepper motor 76 in the current implementation has a resolution of 0.9° per step, so the disc 88 can be positioned in increments of 0.9°. Since the size of the channel 36 directly affects the magnitude of flow, the oscillator 30 adjusts the flow throughout a given procedure. Typically, it is used as follows.

During the insufflation mode, the oscillator 30 modulates the airflow. The disc 88 is rotated to a stationary position of high, medium, or low flow rates. In the high position, the disc 88 is parallel to the channel 36, thus maximizing the channel size. This minimizes the resistance to flow, thereby maximizing the flow rate going to the patient. At the low flow rate, the disc 88 is almost perpendicular to the channel 36, thus minimizing the channel size. This creates the most resistance to flow, thereby minimizing the flow rate to the patient. Adjustment of this airflow setting determines how fast the patient's lungs fill up during inhale.

During exsufflation mode, the oscillator 30 is either inactive or is in a "flutter" mode. If the oscillator 30 is inactive, the disc 88 is rotated until it is parallel to the channel 36 in order to maximize airflow. Since the productiveness of a cough is directly attributable to the magnitude of exsufflation flow, airflow is maximized during exhale.

In flutter mode, the oscillator 30 creates a flow that rapidly changes during exsufflation. To do this, the disc 88 is continuously rotated, causing the channel size to rapidly change from a maximum flow rate to minimal flow rate and back. This airflow rate from maximum to minimum is varied by simply adjusting the rotation frequency. "Fluttering" the flow rate during exsufflation assists in the dislodging of mucus in the pulmonary airways.

As indicated above, the size of the channel 36 directly affects the airflow. In the present implementation, the size of the channel 36 is 19.6 mm, which is measured at the inside diameter at the connector port 62 of the oscillator 30. The blower 14 is capable of providing a flow rate of up to 12.4 liters/sec. The airflow is affected by the length and diameter of the channel 36 between the blower and the patient, as well as the position of the disc 88 in the oscillator 30. Due to the parameters of the channel 36 in the present implementation, air flow dramatically decreases by the time it reaches the patient. In the present implementation, a flow rate of 12.4 liters/sec at the blower 14 results in a flow rate at the patient of about 9 liters/sec. The minimum flow to create a productive cough is about 6 liters/sec (mean peak expiratory flow rate) at the patient.

The controller 20 has a processor 102 which includes its attendant clock, memory, input/output devices, etc. The processor 102 sends signals to drivers that provide control signals to various components. Various sensors notify the processor 102 of the conditions within the apparatus 10. The processor 102 controls the blower 14 through a power driver 108 and a speed driver 110. The processor 102 controls the direction valve 28 through the direction valve motor driver 104 and the direction valve position encoder 124. The processor 102 controls the oscillator 30 through the oscillator motor driver 106 and the oscillator position encoder 126. Other sensors include the blower temperature sensor 112, the channel air temperature sensor 116 and the channel air pressure sensor 120. The speaker 26, mounted on the floor of the case 12, is controlled by the speaker driver 122 and the touch screen 24 is controlled by the touch screen driver 128. The touch screen 24 is a display as well as a user input device.

The power supply 22 provides power to the apparatus 10 through an AC power cord connected to the power input connector 78. Optionally, the power supply 22 is capable of providing power from an internal battery 92 or an external DC source, such as an automobile power outlet or external battery, through a DC source connector 94.

Optionally, the apparatus 10 includes a remote control 96. The remote control 96 can be wired, as in FIG. 2, or wireless. The wired remote control plug 99 plugs into the apparatus 10 through a remote control jack 98. The remote control 96 operates all or a subset of the functions of the apparatus 10. The simple remote control 96 of FIG. 2 has a single rocker switch 97 to control an insufflate/exsufflate cycle. The remote control 96 can be hand operated or foot operated.

Software running on the processor 102 controls the operation of the apparatus 10. The software controls the treatment cycles and a cycle is defined as an insufflation, an exsufflation, and a rest. A treatment cycle has a number of settable parameters associated with it, as follows.

The manual/automatic setting determines whether the apparatus 10 is to operate in manual mode or automatic mode. In manual mode, the user controls when and how a treatment cycle occurs by pressing the associated buttons on the touch screen 24 or on the remote control 96. In automatic mode, the apparatus 10 repeatedly initiates treatment cycles. For both modes, the user can set insufflation/exsufflation pressures, flow, and flutter.

Figure 7:
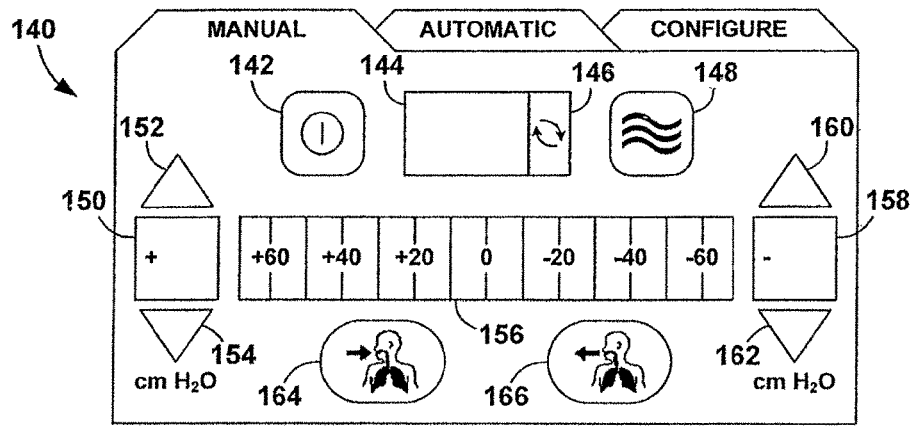
FIG. 7 is an example display for manual mode.

Shown in FIG. 7 is an example display 140 for manual mode.

The insufflation pressure 150, the positive pressure of the air being pushed into the lungs, can be set in the range of 0-50 cmH$_2$O in 1 cmH$_2$O increments using an increase arrow 152 and decrease arrow 154. The exsufflation pressure 158, the negative pressure of the air being pulled from the lungs, can be set in the range of 0-50 cmH$_2$O in 1 cmH$_2$O increments using an increase arrow 160 and decrease arrow 162.

The flow rate can be set to high, medium, or low via button 148. In high, the disc 88 sits parallel to the channel 36, maximizing the flow rate to the patient. In medium, the disc 88 sits at about 45° to the channel 36. In low, the disc 88 sits almost perpendicular to the channel 36, minimizing the flow rate to the patient. The flow rates are relative to the exhale flow setting. If the insufflation pressure setting is high, the flow will be high. If the insufflation pressure setting is low, the flow will be correspondingly low.

Figure 8:
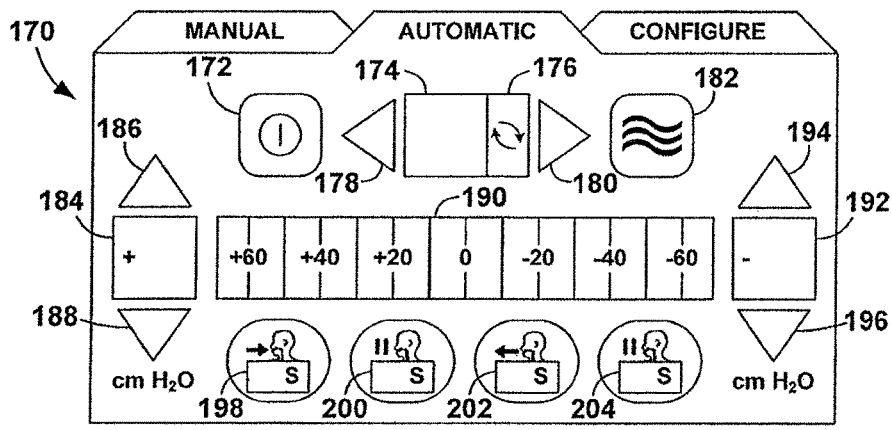
FIG. 8 is an example display for automatic mode.

Shown in FIG. 8 is an example display 170 for automatic mode.

The insufflation pressure 184 can be set in the range of 0-50 cmH$_2$O in 1 cmH$_2$O increments using an increase arrow 186 and decrease arrow 188. The exsufflation pressure 192 can be set in the range of 0-50 cmH$_2$O in 1 cmH$_2$O increments using an increase arrow 194 and decrease arrow 196. The flow rate can be set to high, medium, or low via button 182.

The insufflation time 198, the length of time that the positive insufflation pressure is active, can be set in the range of 0-3 sec in 0.2 sec increments. The exsufflation time 202, the length of time that the negative exsufflation pressure is active, can be set in the range of 0-3 sec in 0.2 sec increments. The rest time 204, the length of time between exsufflation of one cycle and insufflation of the next cycle, can be set in the range of 0-3 sec in 0.2 sec increments. The number of cycles 174 can be set in the range of 1-99 using decrement arrow 178 and increment arrow 180.

Figure 9:
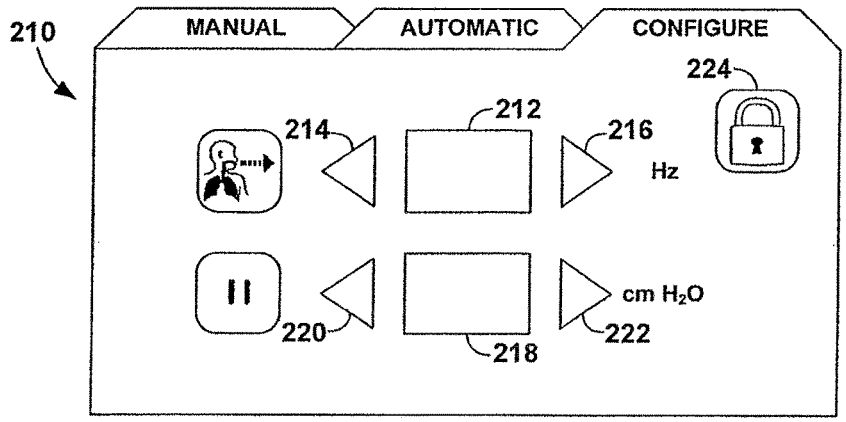
FIG. 9 is an example display for configuration.
Figure 10:
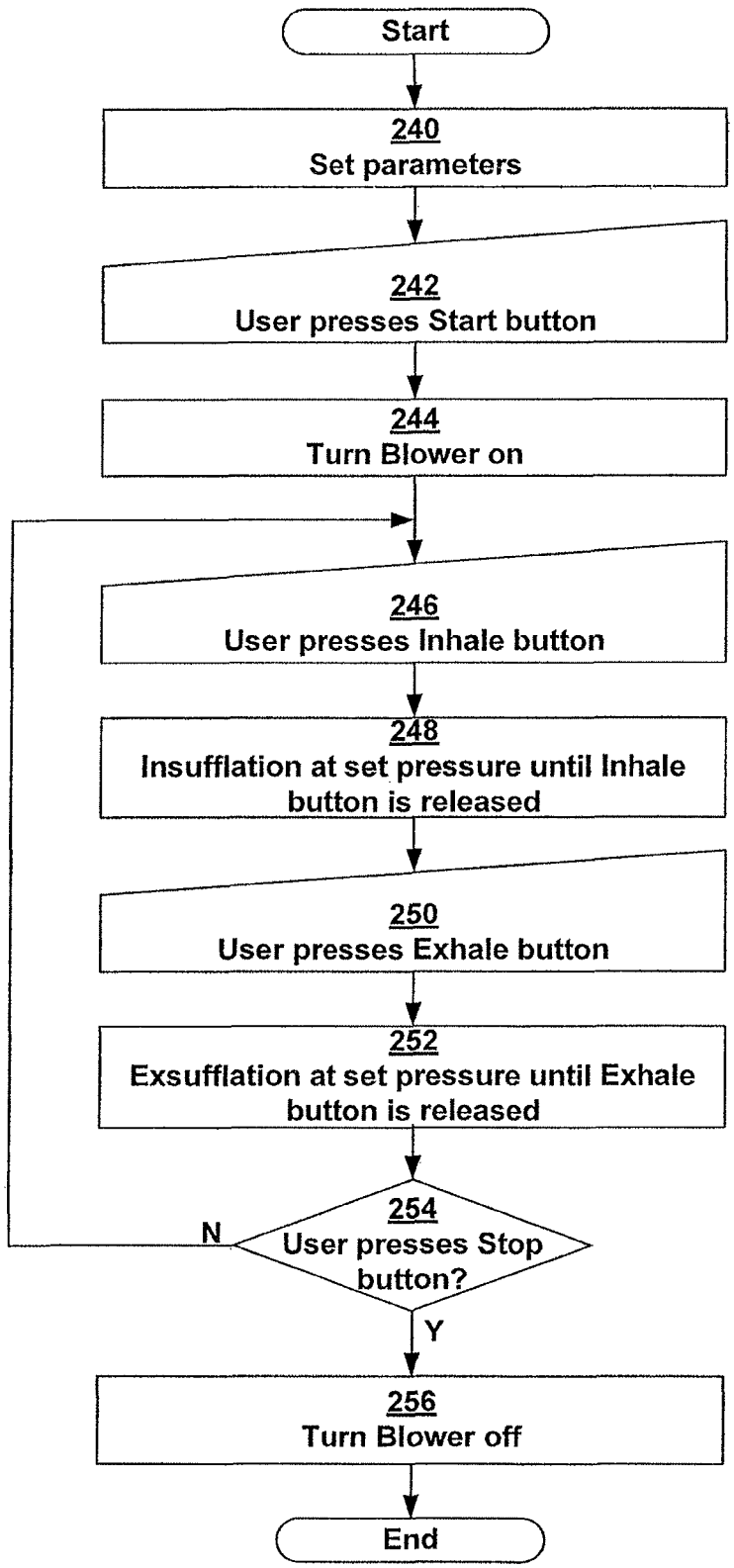
FIG. 10 is a flow diagram of the operation of the apparatus in manual mode.
Figure 11:
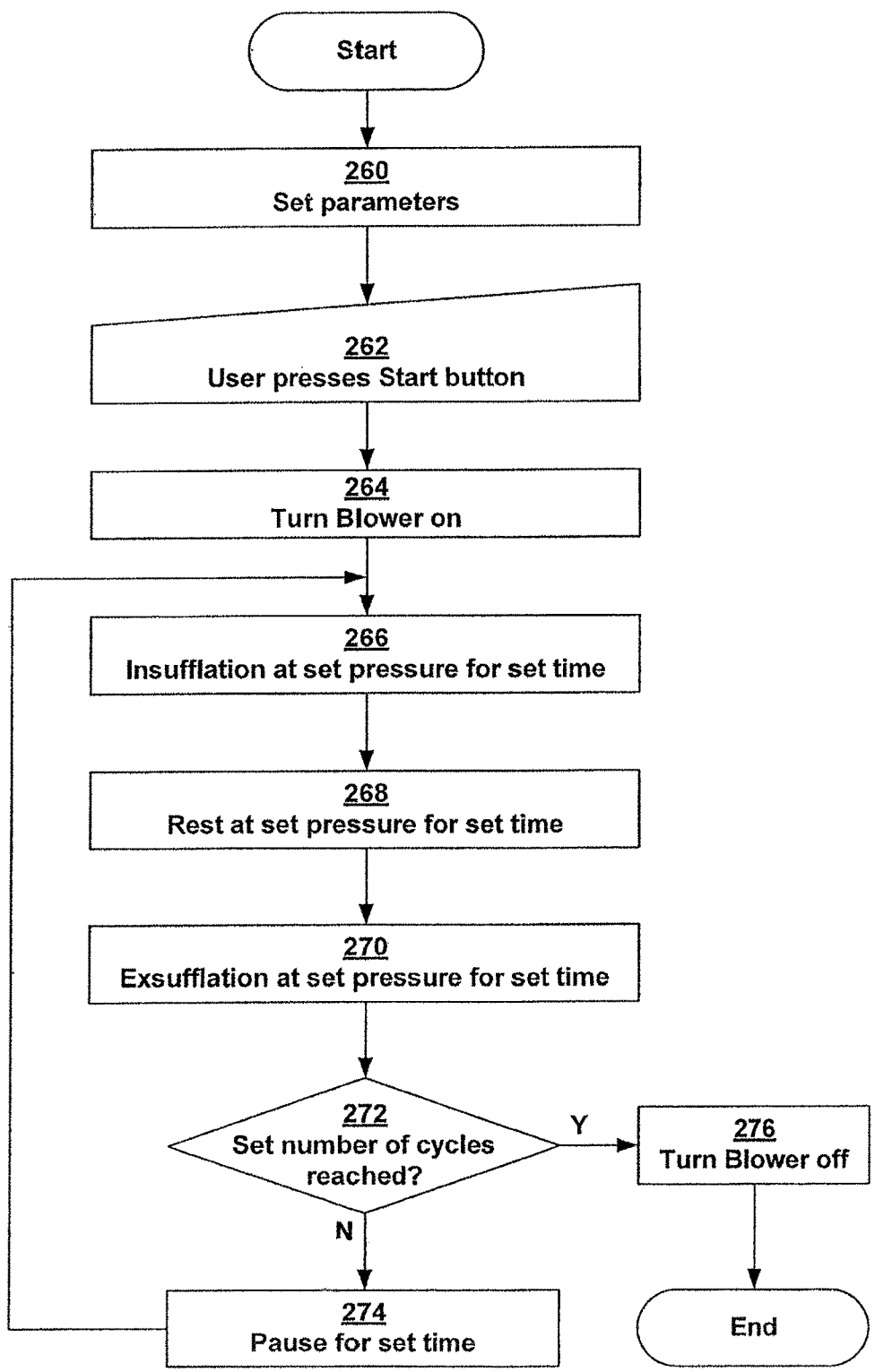
FIG. 11 is a flow diagram of the operation of the apparatus in automatic mode.

Shown in FIG. 9 is an example display 210 for configuration.

The resting positive pressure 212, the positive pressure set during rest when neither insufflation nor exsufflation is active, can be set in the range of 0-15 cmH$_2$O in 1 cmH$_2$O increments using an increase arrow 214 and decrease arrow 216.

The user can enable or disable flutter and set the flutter rate 218 in the range of 0-20 Hz in 1 Hz increments using an increase arrow 220 and decrease arrow 222. Flutter is disabled when the flutter frequency 218 is zero. During insufflation, the oscillator disk 88 is positioned in a fixed orientation based on the flow setting. During exsufflation, the oscillator 30 behavior is based on whether flutter is enabled or disabled. If enabled, the oscillator disk 88 rotates continuously at the set flutter rate. If flutter is disabled, the oscillator disk 88 is positioned parallel to the channel 36, thereby maximizing flow.

The user can enable or disable a parameter lock. When enabled by pressing the lock button 224, all settings are locked and cannot be changed without entering a password.

The software monitors the various sensors in the system: the blower temperature sensor 112, the channel air temperature sensor 116, and the channel air pressure sensor 120. When any of the sensors indicate that there is a problem, such as an out-of-range temperature or pressure, the system is immediately switched into an idle state, shutting off the blower, and a message is posted on the display 24 indicating the error.

The software displays information to the user on the touch screen 24 and the user uses the touch screen 24 to set operating parameters in ways known in the art. For example, if the user wishes to set the insufflation pressure, the user touches the insufflation pressure display on the touch screen 24 and the display changes to show up and down arrows. The user touches the appropriate arrow repeatedly until the desired setting is reached, the up arrow to increase the pressure and the down arrow to decrease the pressure. All parameter settings operate similarly.

As indicated above, the apparatus 10 has a manual mode and an automatic mode. In manual mode, several parameters must be set prior to operation, as at 240. These parameters include the insufflation pressure 150, the exsufflation pressure 158, the flow rate 148, and the flutter 212 during exsufflation. Optionally, the cycle count display 144 is reset to zero using button 146. After the parameters are set, the user touches a start/stop button 142 on the touch screen 24, as at 242, to turn the blower 14 on, as at 244.

An insufflation is initiated by actuating either an inhale button 164 on the touch screen 24 or the appropriate side of the rocker switch 97 on the remote 96, as at 246. Insufflation is maintained until the button 164 or rocker switch 97 is released, as at 248. An exsufflation is initiated by actuating either an exhale button 166 on the touch screen 24 or the appropriate side of the rocker switch 97 on the remote 96, as at 250. Exsufflation is maintained until the button 166 or rocker switch 97 is released, as at 252. At the end of exsufflation, the cycle count display 144 increments to display the number the cycles since the last reset.

When treatment is complete, the user touches the start/stop button 142 on the touch screen 24, as at 254, to turn the blower 14 off, as at 256.

In automatic mode, several parameters must be set prior to operation, as at 260. These parameters include the insufflation pressure 184, the exsufflation pressure 192, the insufflation time 198, the exsufflation time 202, the rest time 204, the flow rate 182, the flutter during exsufflation 212, and the number of treatment cycles 174. Optionally, the cycle count display 174 is reset to zero via button 176.

After the parameters are set, the patient touches a start/stop button 172 on the touch screen 24, as at 262, to turn the blower 14 on, as at 264, and to begin the treatment cycles. As described above, a treatment cycle includes an insufflation at the set insufflation pressure for the set insufflation time, as at 266, a exsufflation at the set exsufflation pressure for the set exsufflation time, as at 268, and a rest at the set rest pressure for the set rest time, as at 272. At the end of the exsufflation, the cycle count display 174 increments to display the number the cycles since the last reset. When the set number of the treatment cycles is reached, as at 270, the apparatus 10 discontinues treatment and turns the blower 14 off, as at 274. If the user wishes to abort treatment prior to reaching the end of the last treatment cycle, the user touches the start/stop button 172 on the touch screen 24.

Thus it has been shown and described an apparatus for inducing coughs which satisfies the objects set forth above.

Since certain changes may be made in the present disclosure without departing from the scope of the present invention, it is intended that all matter described in the foregoing specification and shown in the accompanying drawings be interpreted as illustrative and not in a limiting sense.

The invention claimed is:

1. An apparatus comprising
a blower having an intake and an exhaust,
a patient interface,
at least one valve having an insufflation position to couple the exhaust of the blower to the patient interface so that a positive insufflation pressure is applied to an airway of a patient via the patient interface, the at least one valve having an exsufflation position to couple the intake of the blower to the patient interface so that a negative exsufflation pressure is applied to the airway of the patient, and
a controller to control operation of the blower and the at least one valve, wherein the apparatus has an automatic mode in which the controller switches the at least one valve between the insufflation position and the exsufflation position based on at least one preselected time interval, wherein the apparatus has a manual mode in which the controller switches the at least one valve between the insufflation position and the exsufflation position based on a manual input, wherein the apparatus has a rest mode in which the controller positions the at least one valve in the insufflation position and operates the blower such that a positive rest pressure that is less than the positive insufflation pressure is applied to the airway of the patient.

2. The apparatus of claim 1, wherein the intake of the blower is operationally connected to atmosphere when the valve is in the insufflation position.

3. The apparatus of claim 1, wherein the manual input is usable to select the rest mode.

4. The apparatus of claim 1, wherein said blower comprises a variable speed blower and the parameter settings further include a blower speed.

5. The apparatus of claim 1, wherein said parameter setting further include at least one of an insufflation time, an exsufflation time, and a rest time.

6. The apparatus of claim 1, wherein the manual input comprises an inhale button coupled to the controller and an exhale button coupled to the controller, the valve being in the insufflation position in response to the inhale button being actuated, and the valve being in the exsufflation position in response to the exhale button being actuated.

7. The apparatus of claim 6, wherein said apparatus is in a rest mode when neither the inhale button nor the exhale button are actuated.

8. The apparatus of claim 1, further comprising a case in which the blower, the valve, and the controller are housed.

9. The apparatus of claim 8, further comprising a remote control jack coupled to the controller and accessible at an exterior of the case and further comprising a remote control that is removably coupleable to the remote control jack.

10. The apparatus of claim 9, wherein the remote control include a rocker switch that is movable to control whether the apparatus is in the insufflation mode or the exsufflation mode.

11. The apparatus of claim 1, further comprising a stepper motor that is signaled by the controller to control whether the valve is in the insufflation position or the exsufflation position.

12. The apparatus of claim 1, further comprising a temperature sensor coupled to the controller, the temperature sensor being positioned so as to measure a temperature of the blower.

13. The apparatus of claim 1, further comprising a temperature sensor coupled to the controller, the temperature sensor being positioned so as to measure a temperature of air flowing toward the patient interface.

14. The apparatus of claim 1, further comprising a pressure sensor coupled to the controller, the pressure sensor being positioned so as to measure a pressure of air flowing toward the patient interface.

15. An apparatus comprising
a blower having an intake and an exhaust,
a patient interface,
at least one valve having an insufflation position to couple the exhaust of the blower to the patient interface so that a positive insufflation pressure is applied to an airway of a patient via the patient interface, the at least one valve having an exsufflation position to couple the intake of the blower to the patient interface so that a negative exsufflation pressure is applied to the airway of the patient,
a controller to control operation of the blower and the at least one valve, wherein the apparatus has an automatic mode in which the controller switches the at least one valve between the insufflation position and the exsufflation position based on at least one preselected time interval, wherein the apparatus has a manual mode in which the controller switches the at least one valve between the insufflation position and the exsufflation position based on a manual input,
a case in which the blower, the at least one valve, and the controller are housed,
a remote control jack coupled to the controller and accessible at an exterior of the case, and
a remote control that is removably coupleable to the remote control jack.

* * * * *